(12) United States Patent
Friesner et al.

(10) Patent No.: US 9,858,395 B2
(45) Date of Patent: Jan. 2, 2018

(54) BINDING AFFINITY SCORING WITH PENALTY FOR BREAKING CONJUGATION BETWEEN AROMATIC LIGAND GROUPS

(75) Inventors: Richard A. Friesner, New York, NY (US); Robert Murphy, Jamul, CA (US)

(73) Assignee: Schrodinger, LLC, New York, NY (US)

( * ) Notice: Subject to any disclaimer, the term of this patent is extended or adjusted under 35 U.S.C. 154(b) by 1092 days.

(21) Appl. No.: 13/113,506

(22) Filed: May 23, 2011

(65) Prior Publication Data

US 2012/0303292 A1   Nov. 29, 2012

(51) Int. Cl.
*G06F 19/00* (2011.01)
*G06F 19/10* (2011.01)

(52) U.S. Cl.
CPC .................. *G06F 19/706* (2013.01)

(58) Field of Classification Search
None
See application file for complete search history.

(56) References Cited

U.S. PATENT DOCUMENTS

| | | |
|---|---|---|
| 2005/0119837 A1 | 6/2005 | Prakash et al. |
| 2007/0061118 A1 | 3/2007 | Friesner et al. |
| 2007/0078605 A1 | 4/2007 | Diller et al. |
| 2008/0312894 A1 | 12/2008 | Friesner et al. |
| 2010/0057797 A1 | 3/2010 | Pitman et al. |

FOREIGN PATENT DOCUMENTS

| | | |
|---|---|---|
| WO | WO 2006/099178 | 9/2006 |
| WO | 2008/141260 | 11/2008 |

OTHER PUBLICATIONS

Glide 5.5 User Manual (2009) Schrodinger Press; Schrodinger, LLC:1-126.*
Kinnings et al. Journal of Chem. Inf. Model. (2011) vol. 51(2):408-419.*
Stornaiuolo et al. Nature Communications (2013) vol. 4:1-11.*

(Continued)

*Primary Examiner* — Lori A Clow
(74) *Attorney, Agent, or Firm* — Fish & Richardson P.C.

(57) ABSTRACT

A method of scoring binding affinity of a proposed ligand molecule for a receptor molecule using computer analysis and computer data bases to accounts for the increase in energy required where docking disrupts or partially disrupts the π-conjugated character of the ligand when bound to the receptor. The method uses data representing one or more proposed ligand molecules to be scored and data representing the receptor molecule. Computer analysis of the proposed ligand molecule data determines whether the ligand includes at least one π-conjugated moiety having multiple possible geometries, one of those geometries being characterized by less delocalization of electrons across the π-conjugated moiety than the delocalization of electrons characterizing another of those geometries. Computer analysis of the predicted ligand-receptor structure determines whether the ligand in the ligand-receptor structure adopts the geometry characterized by less delocalization. If so, a penalty is explicitly imposed for reduced delocalization of electrons across the π-conjugated moieties.

22 Claims, 1 Drawing Sheet

(56) References Cited

OTHER PUBLICATIONS

Nevins et al., Molecular Mechanics (MM4) Calculations on Conjugated Hydrocarbons, Journal of Computational Chemistry, vol. 17, Nos. 5 & 6, 695-729 (1996).
Gilson, et al; "Calculation of Protein-Ligand Binding Affinities"; *Annual Review of Biophysics and Biomolecular Structure*; vol. 36, No. 1; Jun. 1, 2007; pp. 21-42.
Krammer, et al.; "LigScore: a novel scoring function for predicting binding affinities"; *Journal of Molecular Graphics and Modelling, Elsevier Science*; vol. 23, No. 5, Apr. 1, 2005; pp. 395-407.
Kitchen, et al.; "Docking and Scoring in Virtual Screening for Drug Discovery: Methods and Applications"; *Nature, Reviews*, vol. 3, Nov. 1, 2004; pp. 935-949.
European Communication; EP Appln. No. 12789317.0; dated Dec. 10, 2014; 5pp.
Supplemental European Search Report; EP Appln. No. 12789317.0; dated Nov. 13, 2014; 4 pp.
Drug Design; https://en.wikipedia.org/wiki/Drug_design; retrieved on Jul. 14, 2016; 9 pp.
Moroney; Drug Action; http://www.merckmanuals.com/home/drugs/drug-dynamics/drug-action; Merck Manual; retrieved on Jul. 14, 2016, 2 pages.

\* cited by examiner

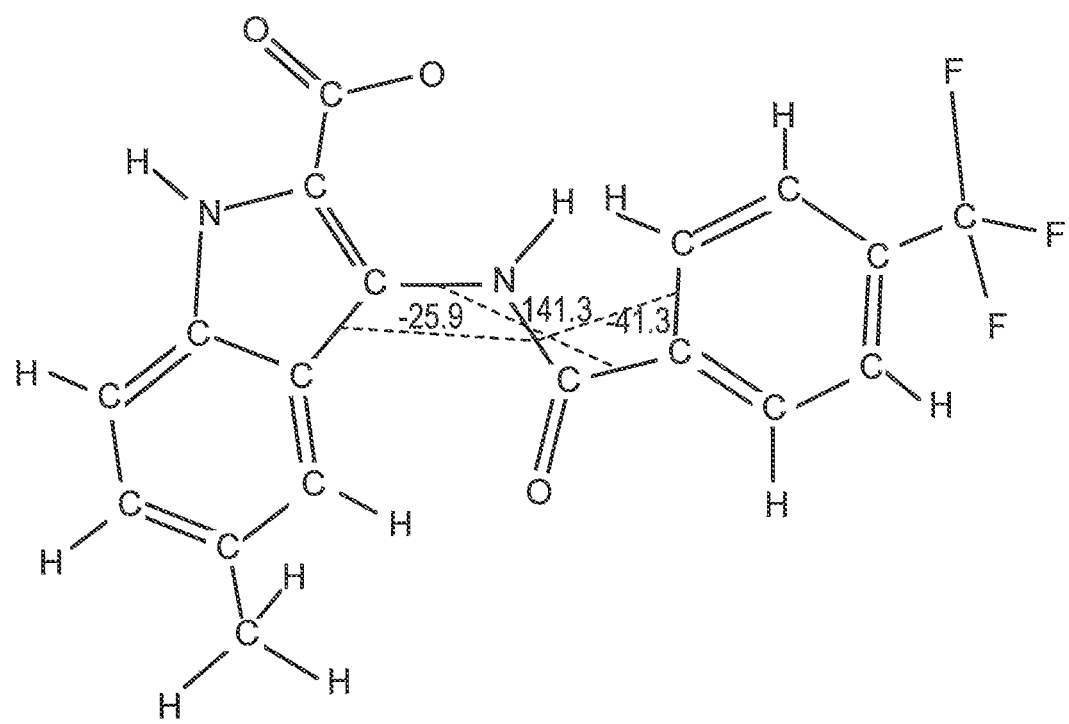

BINDING AFFINITY SCORING WITH PENALTY FOR BREAKING CONJUGATION BETWEEN AROMATIC LIGAND GROUPS

TECHNICAL FIELD

The invention is in the general field of computer-based methods for estimating binding affinity between a ligand and a receptor molecule.

BACKGROUND

Many drugs operate by chemically binding to specific molecular receptors. Molecular receptors typically are proteins (a term that includes glycoproteins and lipoproteins) in an animal such as a human being, and drug design and selection can be facilitated by accurately estimating the binding affinity of a drug to a protein, or, more generally, estimating the binding affinity of a ligand to a receptor, the term receptor being used to mean any moiety that specifically binds the ligand.

One way to determine receptor-ligand binding affinity uses the molecular structure that results when the ligand binds to the receptor ("the ligand-receptor complex"). Such structures may be studied by x-ray crystallography. The publicly accessible protein data bank (PDB) now contains more than 70,000 x-ray crystal structures, and pharmaceutical and biotechnology companies have an order of magnitude more proprietary structures. Many of these structures have been co-crystallized with small molecules bound to them. The examination of such structures, and deployment of the knowledge thereby gained to design new, more potent, and more specific inhibitors, is referred to as structure-based drug design.

Computational modeling facilitates structure-based drug design. One aspect of modeling detailed below involves scoring functions that use simulation techniques, such as molecular dynamics, Monte Carlo, or continuum electrostatics calculations. Scoring functions can be problematic when one is required to calculate a very small difference (the binding affinity) between two very large numbers (the free energies of the complex and of the separated protein and ligand). An alternative approach is to develop an empirical scoring function, based on the geometry of the complex, which directly evaluates the desired quantity. Such an approach has the advantage of being extremely fast as well as being amenable to fitting large amounts of which are now publicly available to experimental data. Commonly owned US 2007/0061118 A1 "Predictive scoring function for estimating binding affinity" (hereby incorporated by reference in its entirety) discloses such scoring functions.

It is desirable to increase the accuracy and robustness of scoring functions by making material improvements in the functional form that better reflect physical reality. Various patent applications that are commonly owned with this application describe ways to improve scoring functions: WO/2008/141260, entitled "Binding Affinity Scoring Function Including Factor For Environs Of Ring or Bulky Rigid Group"; U.S. Ser. No. 13/079,725, filed Apr. 4, 2011 entitled "Binding Affinity Scoring Function Penalizing Compounds which Make Unfavorable Hydrophobic Contacts With Quasilocalized Water Molecules in the Receptor Active Site"; and U.S. Ser. No. 13/079,489, filed Apr. 4, 2011 entitled "Scoring Function Penalizing Compounds which Desolvate Charged Protein Side Chains Structure". Each of the above commonly owned applications is hereby incorporated by reference in its entirety.

A second major problem with scoring functions is that they may assign better (more negative) binding affinity scores to inactive compounds (i.e. compounds that would not be determined to bind to the receptor in a typical experimental screening protocol) than to active compounds. If a large number of inactive compounds are ranked ahead of active compounds, a principal function of docking—to discover new active compounds against a specified receptor from a very large compound library (often millions of compounds)—becomes difficult to carry out effectively. Therefore, substantially reducing the number of "false positives" (ranking of inactive compounds as active) would greatly improve scoring function performance.

SUMMARY

We have discovered an improved computer implemented method of scoring binding affinity of a proposed ligand molecule for a receptor molecule. The method uses computer analysis and computer data bases to accounts for the increase in energy required where docking disrupts or partially disrupts the $\pi$-conjugated character of the ligand when bound to the receptor. The method uses data representing one or more proposed ligand molecules to be scored and data representing the receptor molecule. Computer analysis of the proposed ligand molecule data determines whether the ligand includes at least one $\pi$-conjugated moiety having multiple possible geometries, one of those geometries being characterized by less delocalization of electrons across the $\pi$-conjugated moiety than the delocalization of electrons characterizing another of those geometries. Computer analysis of the predicted ligand-receptor structure determines whether the ligand in the ligand-receptor structure adopts the geometry characterized by less delocalization. If so, a penalty is explicitly imposed for reduced delocalization of electrons across the $\pi$-conjugated moieties.

In preferred embodiments, computer analysis of the ligand determines whether the ligand has one or more rotatable bond paths connecting two chemical moieties which are capable of significant $\pi$ electron delocalization between the groups across the rotatable bond. The method then determines the configuration of the ligand in a ligand-receptor complex, and, for at least one rotatable bond path, it determines whether the geometry of the docking configuration substantially reduces electron delocalization of an energetically accessible ligand geometry in solution or in the gas phase. For example the method determines whether the $\pi$-conjugated moiety includes at least one rotatable bond whose rotation changes the extent of delocalization of electrons across the $\pi$-conjugated moiety. The $\pi$-conjugated moiety may include at least one aromatic ring. The magnitude of the penalty may be set at an amount intended to generally reflect the reduction of electron delocalization between the configuration of the proposed ligand when complexed with the receptor and the delocalization of an uncomplexed, more delocalized, configuration of the proposed ligand. Often, the $\pi$-conjugated moiety is more planar in the configuration characterized by greater delocalization than it is in the configuration characterized by less delocalization. In specific embodiments, the energies of the configurations of the $\pi$-conjugated moiety may be measured by one or more of: a) a molecular mechanics force field, b) quantum chemical methods, or c) deviations from planarity. When using the latter measurement, those skilled in the art will understand how to measure planarity. For example it may be measured by the values of the torsional angles in the conjugated path. Effectively zero degrees or 180 degrees is full planarity. Deviations from these angles imply deviations from planarity. A 90 degree angle implies the maximum deviation from planarity.

Also in preferred embodiments, clashes between atoms that form internal hydrogen bonds may be ignored. The ligand may include multiple conjugated rotatable bond paths and a penalty is assessed for each bond path where the ligand in the ligand-receptor structure adopts the geometry characterized by less delocalization. A conformational search method may be used to investigate the energy of at least one conformation of the ligand in solution or in the gas phase and to identify a confirmation exhibiting conjugation between the moieties connected by the rotatable bond path. The degree of conjugation along the rotatable bond path may be determined by the deviation from planarity of the moieties connected by the rotatable bond path. A molecular mechanics force field may be used to calculate the energies of the various conformations in the conformational search. Quantum chemical methods may be used to calculate the energies of the various conformations in the conformational search. A simplified interaction model—such as one enforcing minimum allowed distances between atoms of various types and basing the conjugation energy upon deviation from planarity—may be used to evaluate the energetics of the various conformations in the conformational search. The magnitude of the penalty may be determined by the degree of distortion of the ligand conformation in the docked complex from a low energy conformation in solution or in the gas phase. A penalty of zero may be assigned to a conjugated rotatable bond path if the lowest energy conformation in solution or in the gas phase does not enable substantial conjugation between the two moieties connected by the conjugated rotatable bond path, due to large deviation from planarity.

One way to enumerate aromatic bond paths is to identify aromatic atoms and to enumerate the bond paths from the connectivity of the identified aromatic atoms. Rotatable bonds along aromatic bond paths are then identified and torsion angles of rotatable bonds are computed. The penalty may be estimated from the values of torsion angles. In one embodiment, aromatic atom types composing $\pi$-conjugated moiety are identified, aromatic bond paths within a $\pi$-conjugated moiety are enumerated, aromatic rotatable bonds lying along these aromatic bond paths are identified, torsion angles of these aromatic rotatable bonds are computed, and a free energy penalty is computed as a function of the torsion angles.

The invention also features computer readable media storing instructions which cause a computer to perform the method of claim 1.

Other features and advantages of the invention are apparent from the following description, and from the claims.

BRIEF DESCRIPTION OF THE DRAWINGS

FIG. 1 Decoy molecule 681094 depicted here suffers a penalty to the dihedral angles adopted by the molecule across a conjugated moiety. The specific dihedrals leading to the penalty are labeled with dashed lines.

DETAILED DESCRIPTION

Practicing the invention begins with a receptor (or "target", typically a protein) structure that has sufficient resolution to permit the use of computational software to "dock" a small molecule ligand into the correct position and orient it in the receptor active site cavity and to calculate a binding affinity of the ligand given this structure. Computer software programs that perform this task are referred to as "docking" programs.

A docking program typically carries out two distinct tasks to model receptor-ligand binding. First, a structure of a receptor-ligand complex is predicted. When this assumption fails, a different structure of the receptor as a starting point is used. The problem of constructing alternative receptor structures that are modified to accept ligands requiring a substantial change in receptor conformation ("induced fit") is a very important one.

Various adequate receptor-ligand structure prediction programs are well known and can be used for the starting point, and those in the art will understand that the invention described herein can generally be used with receptor-ligand prediction programs. Examples of such functions that are readily available include: Glide, GOLD, FRED, FlexX, or AutoDock, among many others.

Once in possession of a receptor structure in reasonable agreement with experimental data, the second task of the docking program is to calculate a receptor-ligand binding affinity, given as an input the docked structure. A mathematical function employed to calculate the binding affinity (or a contribution thereto) is referred to as a "scoring function." Improvements to such scoring functions for calculating receptor-ligand binding affinity are the subject of this invention.

The estimates of receptor-ligand binding affinities described below are applicable when a structure of the receptor-ligand complex is represented by a suitable structural model. There are a number of ways to characterize the quality of structural models of receptor-ligand complexes, so long as the model adequately agrees with experimental data. Measures of structural agreement such as RMSD, DME, or SIFt score among others might be used. Accurate scores are typically but not exclusively obtained using: i) a small root mean square deviation (RMSD) from the experimental structure (typically less than 2 Angstroms, although the required value will vary depending upon details of the complex), ii) recognition of the formation of substantially all hydrogen bonds seen in the experimental complex, iii) appropriate placement of substantially all hydrophobic groups in the correct receptor cavities, and iv) the absence of incorrect structural or electrostatic clashes that could lead to the assignment of substantially incorrect penalty terms. Since relative binding affinity of ligands to a given receptor is under consideration, a constant offset, as is in many cases engendered by reorganization energy of the receptor active site to accommodate the ligand, has no effect on practical applications.

In many (although not all) cases, the receptor can adopt more than one fundamentally different conformation in response to a class of ligands (e.g., DFG-in and DFG-out binders to p38 map kinase); to compare the binding free energies in such cases, different core reorganization parameters may be required for the different receptor conformations. Where calculation of these parameters is not practical from first principles they are treated as adjustable, receptor specific parameters. Other parameters are however contained in a global model which is not receptor-specific or even specific to a particular class of receptors.

The present invention improves the ability of the scoring function to discriminate between inactive and active compounds against a given receptor. While active compounds for a wide range of receptors are readily found in the Protein Data Bank (PDB), our data below validating the invention also assessed known inactive compounds as a negative control. Accessing known inactive compounds from publicly available data is challenging. Therefore, we have devised an alternative protocol which is based on the use of a random library of 1000 drug-like compounds. These compounds are docked into a conformation of the receptor, and predicted binding affinities are obtained for each compound using various proposed improvements to the scoring function.

Our scoring function is calibrated so that active compounds achieve scores that are typically close to experimental binding affinities, with a standard deviation of approximately 1 log unit of binding affinity (~1.5 kcal/mole). An experimental "hit" in a random screen in the pharmaceutical industry is generally taken to have a binding affinity of ~7.0 kcal/mole or more (~10 µm concentration). Given the intrinsic fluctuations in the scoring function of 1.5-2.0 kcal/mole, we set the computational threshold for estimating hits at a score of −9.0 kcal/mole; thus any compound in the random 1000 compound library which scores −9.0 or less is predicted to be a hit. Other compounds in the −7.0 to −9.0 range are predicted as possible hits as well, but such scores may also be due to the noise in the scoring function which we are unable at present to reduce further (in part due to limitations on the publicly available experimental data). Hence, we focus in developing our improvements on ensuring that the number of random compounds scoring more negatively than −9.0 is compatible with experimental hit rates for random drug-like compound libraries.

The hit rate for experimental screens will vary depending upon the receptor, but an illustrative "average" hit rate is 0.5%, or 5 compounds out of 1000. Thus, if substantially more than 5 compounds achieve a score of −9.0 kcal/mole, the assumption is made that inactive compounds are receiving scores that are too favorable.

In such a situation, the scoring function may be improved by adding positive "penalty" terms which reduce the magnitude of the predicted binding affinity. Such terms represent physical processes which make binding less favorable. An example of a process of this type would be a desolvation in which a polar group of the protein or ligand is blocked by nonpolar groups of the ligand and loses access to water. This results in a large loss in free energy, making the compound inactive. If the loss of free energy is sufficiently large, then such penalties will only rarely (if at all) be observed in complexes with active compounds. This means that the new terms must be derived by examining the structures produced when the random library is docked into the receptor.

The invention described herein is designed to identify a particular type of geometry for which a large ligand strain energy, substantially larger than that present in the great majority of active compounds in the Protein Data Bank, can be assigned. The geometry involves rotation about a bond within a π-conjugated moiety of a ligand, typically composed by 1 or more aromatic (sub)moieties. In this situation, in the appropriate geometry, electrons are delocalized across the π-conjugated moiety in a rigorous quantum mechanical description, which lowers the energy of this geometry as compared to alternative geometries which disrupt the delocalization of electrons across the π-conjugated moiety. When the geometry of the active site may force the ligand into a non-optimal geometry with reduced electron delocalization across the π-conjugated moiety, a large amount of strain energy is introduced, and a substantial penalty e.g., 4 kcal/mole is applied.

Applying the above criterion would be relatively simple, once aromaticity and bond paths preserving conjugation are defined, if the ligand consisted only of the two conjugated groups, and these groups did not interact except through the conjugation. In this case, the ideal geometry to lower the energy via conjugation is planar, and deviations from planarity would be penalized according to the magnitude of the deviation. However, for many ligands, the situation is much more complicated due to other interactions, such as steric repulsions, hydrogen bonds, which perturb the ideal geometry. Steric repulsion in the planar geometry can destabilize this geometry and shift the minimum energy to a nonplanar geometry. Hydrogen bonding can stabilize a geometry which enables the hydrogen bond. The invention described below uses mathematical algorithms to identify atom types and then explores the various possible geometries around the possibly strained bond, using empirical algorithms to estimate the free energy as a function of the torsion angle in question (which in many cases involves searching other, coupled degrees of freedom as well). If it is determined that the geometry of the ligand in the receptor (obtained, e.g., from docking, from other types of simulations, or from experiments such as x-ray crystallography) loses significant conjugation energy as compared to what is possible in solution (the latter is affected by the steric repulsion and hydrogen bonding terms), then an aromatic conjugation penalty is applied.

The above energetic penalty could in principle be assigned by carrying out quantum mechanical calculations, or via a highly accurate molecular mechanics force field. However, the relevant quantum chemical calculations can be very expensive computationally (particularly since many geometries may have to be examined for a given ligand), and, at present, molecular mechanics force fields do not reliably describe conjugation energies for a wide range of ligand chemistry. The invention provides a very fast solution to this critical problem (approximately >15% percent of ligands in a random database of 1 million drug-like molecules have at least one bond which potentially provides a conjugation path between two aromatic groups) and, as shown below, is very successful in targeting random as opposed to known active compounds for a wide variety of receptors.

Details of the preferred algorithm representing the invention are as follows but other algorithms may be used which effect the steps of the invention described here.

1) Assign the following atoms as aromatic:
   a) Aromatic ring atoms are labeled by atomtyping, group typing or other methods; a check is performed to determine that carbons and nitrogens so labeled don't have more than three connections.
   b) atoms in amide bonds and NH connectors.

2) Assign the following bonds as aromatic rotatable bonds:
   a) any rotatable bond consisting of two aromatic atoms as labeled in 1).
   b) rotatable bond(s) connecting two aromatic rings.

3) Find aromatic paths of rotatable bonds starting from an aromatic ring. This may be done using the aromatic bond list above and the Glide XP™ (available from Schrödinger, LLC, New York, N.Y.) anchor code to search the path of bonds emanating from an aromatic ring. Other methods for path searching are well known to the art such as those described in the general field of applications of graph-theoretical methods and combinatorial-mathematical methods to chemical problems. The path is terminated when a non aromatic connection is reached or a separate aromatic ring is reached. Note that an aromatic path may contain a non rotatable aromatic C=C unit or —N=X— unit. For the purposes of labeled atom-atom contacts save the list of atoms in each path including ring(s).

4) For each path construct a list of torsions along the path using the rotatable bond list of the path as well as atoms connected to these rotatable bonds. Thus each path has an associated list of torsions.

5) For each torsion listed in (4) calculate the torsion angle at the input geometry, this is the value (or 180+this value) needed to rotate the torsion to planarity.

6) For each aromatic path determine if there will be clashes between atoms/rings of the path when all torsions of the path are rotated to planarity. The list of atoms used to check clashes includes atoms in the ring(s), atoms of the rotatable bonds, and atoms connected to the ring/rotatable bond set. Since each torsion satisfies planarity at an angle Θ and an angle=180°+Θ, $2^n$ possible combinations of torsion angles may be sampled by way of such a conformational search analysis to test if one does not involve atom-atom clashes. The cutoffs used for defining clashes (among heavy atom pairs) are as follows.
  a) default of 3.1 Å between heavy atoms
  b) 3.25 Å if one atom is a member of a ring with more than 6 atoms in it.
  c) if one of the atoms is an $SO_2$ oxygen, a cutoff of 3.4 Å is used. The art will understand from this specification that other special cases may be needed.

In certain cases, clashes are ignored. For example clashing atoms must be at least a 1-5 atoms apart in the connection table. Clashes between atoms of that form internal H bonds (e.g. CH to N) are not considered.

If a geometry is produced for which no clashes occur, then the torsion path is kept in the list of torsions to be measured in forming a non-planarity penalty. In some cases only a subset of the whole aromatic path can be rotated to planarity without incurring clashes and in these cases consider just the subset of torsions below (in the penalty function).

Steps 1-6 are preprocessing given the input ligand geometry. While scoring any given pose during docking the following function is evaluated which detects non planar torsions in the paths.

7) For each torsion (i) saved in (6) calculate the torsion angle 'Θ_i'. A simple penalty wtor_i for this torsion is given by;

$$wtor\_i = 0.0 \text{ if } \Theta\_i < \Theta\_o$$

$$wtor\_ = A * abs(sin(\Theta\_i - \Theta\_o))$$

Θ_o is 20 degrees for non-biphenyl like paths and 40 degrees for biphenyl like paths where a biphenyl like path is a single bonded connecting two aromatic rings one of which is of size 6. The value of A will depend on the scaling of other terms, but in this example will be between 5 and 20 (e.g. 10).

The total torsional penalty at a given geometry is simply the sum of the wtor_i.

The efficacy of the above invention is demonstrated in the following fashion. First, we have assembled a test suite of 622 protein-ligand complexes of active compounds. As a control for evaluating the method, the examples below involve known crystal structures available in the Research Collaborative for Structural Bioinformatics' publicly accessible Protein Data Bank ("the PDB"). In carrying out optimization, we use poses docked with Glide XP™, a scoring function generally described e.g., in US 2007/0061118 A1 (hereby incorporated by reference), filtering the (very few) cases for which self-docking yields unsuitable structures. By using docked structures, rather than the crystal structures themselves, in our optimization process, we increase the realism of the model and also enable its use with Glide XP™. The invention can be used with any of a substantial number of commercial scoring functions, including without limitation, FRED, FlexX, or AutoDock The PDB structures can be viewed as a large and diverse training set for the scoring function. The invention does not require the use of ligands for which crystal structures are known, nor does it require the use of Glide XP. Testing of the scoring function under similar conditions can be performed by pharmaceutical and biotechnology companies, using proprietary data sets where crystal structures are available. In carrying out these tests, there is no need to release the structures or even to divulge the name of the receptor; one can simply perform the calculations, and report the ability to rank order the compounds as a correlation coefficient.

These complexes give reasonably accurate structures when the ligand is redocked into its native receptor (e.g., a maximum RMSD of 3.5 Å, with the great majority of RMSD's under 2 Å) and their scores, using Glide XP™ scoring function, are on average within ~1 kcal/mole of the experimental binding affinity. Thus, the scoring function in the absence of the term constituting the invention works well for complexes of active compounds taken from the PDB.

We have added a new term to the Glide XP™ scoring function, representing the above-described penalty, and we have recalculated the binding affinity of all active complexes.

Table 1 reports a list of PDB complexes which are impacted by this term, the experimental binding affinity of each complex (dG), and the calculated binding affinity with (Score_np) and without (Score_p) the new term. It can be seen that there are very few cases where active complexes satisfy the above conditions, but when they do, the applied penalty often significantly improves agreement between theory and experiment. These results demonstrate that types of strain penalized by the invention as described are not generally characteristics of complexes of receptors with active ligand molecules.

TABLE 1

Native pdb ligands significantly (>1 kcal/mol) affected by the aromatic torsion penalty term.

| Pdb_system | Score_np | Score_p | dG |
| --- | --- | --- | --- |
| Aff-47 | −9.6 | −8.4 | −8.5 |
| Cdk2__1h00 | −6.3 | −4.7 | −6.0 |
| Cdk2__1g9x | −9.9 | −8.9 | −7.0 |
| Jnk__2b1p | −12.6 | −10.8 | −11.6 |
| Alr2__2hv5 | −12.1 | −11.1 | −11.4 |
| Lck__2ofv | −14.7 | −12.1 | −13.2 |
| Pde5__3bjc | −9.2 | −8.0 | −9.5 |

Score_np is the unpenalized score and score p the penalized score,
dG is is the experimental free energy of binding.

The second criterion for efficacy of the invention is penalizing random database ligands which are assigned highly favorable scores by the current scoring function. In a 1000 compound random database, it is very unlikely that experimentally one would find a compound with a binding affinity that was tighter than 500 nm, or −9 kcal/mole. Therefore a penalty term is improving discriminatory power when it eliminates compounds with binding affinities as good as or better than −9 kcal/mole without inappropriately penalizing active compounds. Because of the intrinsic fluctuations in the scoring function of 1.5-2 kcal/mole, noted above, we nevertheless expect to see some compounds scoring at the −9.0 kcal/mole level (or a little better); these represent active compounds that experimentally would have binding affinities in the −7.0 to −9.0 kcal/mole range, but which achieve a better score due to the scoring function fluctuations. However, if the experimental hit rate for a 10 micromolar screen is on the order of 0.5% (typical for pharmaceutically interesting targets, although there can be significant deviations in either direction from this value), then one would expect there to be no more than 5 compounds from the random library scoring below −9.0 kcal/mole. Hence reducing the number of such values for the suite of receptors tested below 5, and in general reducing the number as much as possible, is a good measure of the efficacy of the penalty term.

Table 2 displays the number of ligands from our standard 1000 compound random library of drug like molecules whose scores are less than −9 kcal/mole for several different scoring functions and for 24 test receptors. This specific comparison is meaningful when the scores for active compounds are close to the experimental scores for these compounds, so in the first column of Table 2 we present results obtained with Glide XP™ optimized to reproduce the scores of PDB complexes with an average error of ~4 kcal/mole. Penalty terms, such as the current invention, must then be added to this scoring function to improve performance in discriminating active from inactive compounds. An example of such a discriminated decoy molecule is depicted in FIG. 1.

TABLE 2

Number of decoy ligands with scores less than −9 kcal/m for a version of XP without recently developed penalty terms (XP), XP with the newer penalty terms (new XP) and XP with the addition of the aromatic torsion term of this patent (XP_tor). Column four has new_xp without the aromatic torsion penalty term (new_XP_notor)

| Pdb_system | XP_ | newXP | XP_tor | newXP_notor |
|---|---|---|---|---|
| Abl | 24 | 15 | 18 | 20 |
| Alr2 | 18 | 4 | 10 | 8 |
| Jnk | 7 | 2 | 4 | 3 |
| Aur | 2 | 2 | 2 | 2 |
| Cdk2 | 10 | 3 | 8 | 5 |
| Chk1 | 7 | 4 | 5 | 5 |
| Dpp4 | 7 | 1 | 6 | 2 |
| Er | 4 | 0 | 2 | 0 |
| Erk2 | 0 | 0 | 0 | 0 |
| Err | 3 | 2 | 2 | 3 |
| Fviia | 2 | 0 | 0 | 0 |
| Fxa | 0 | 0 | 0 | 0 |
| Hivrt | 11 | 2 | 8 | 7 |
| Hsp90 | 2 | 0 | 0 | 1 |
| Lck | 10 | 3 | 4 | 7 |
| Oppa | 1 | 1 | 1 | 1 |
| Pim1 | 46 | 3 | 28 | 6 |
| Pka | 0 | 0 | 0 | 0 |
| Ppar | 1 | 0 | 0 | 0 |
| Ptp1b | 1 | 1 | 1 | 1 |
| Rho | 5 | 2 | 2 | 5 |
| Throm | 2 | 1 | 1 | 2 |
| Upa | 0 | 0 | 0 | 0 |
| P38 | 0 | 0 | 0 | 0 |

In the second column (newXP), we present results obtained when applying the penalty terms described herein are used in combination with other penalty terms, to the scoring function. This results in a significant reduction in the number of decoys that score −9 and lower. Finally, to isolate the specific performance of the invention described herein, column three (XP_tor) present results of adding the invented term to the scoring function of column 1. The term does not strongly affect every receptor, but there are a significant number of receptors which do demonstrate a measurable, highly relevant improvement. Finally, in column 4 (newXP_tor), we present results of deleting the invention from the overall best practices scoring function presented in column 3.

Taken together, the above data demonstrates that the invention described herein makes a substantial contribution to discriminating active from inactive compounds in the Glide XP empirical scoring function. Similar improvement generally would be achieved by adding the penalty term to other scoring functions. The scoring function, including the invention described here, yields 23/24 receptors with 4 or fewer random database ligands scoring below −9.0. The total number of database ligands scoring below −9.0 kcal/mole that are eliminated by the invention (column 1-column 3), summed over all receptors, is 57, a nontrivial fraction of the total number of ligands achieving this score in the original XP function (column 1).

Other embodiments are within the scope of the following claims.

What is claimed is:
1. A method of screening a plurality of proposed ligand molecules for binding to a known molecular receptor, the method comprising:
for each of a plurality of complexes each comprising a ligand-receptor structure comprising a corresponding one of the proposed ligand molecules and the known molecular receptor, scoring a binding affinity of the corresponding proposed ligand molecule to the known receptor using a computer and computer stored data, wherein the scoring comprises:
a) receiving, by one or more computers, data representing one or more of the proposed ligand molecules to be scored,
b) receiving, by one or more computers, data representing a predicted structure of the ligand-receptor structure between the known molecular receptor and the corresponding proposed ligand molecule,
c) scoring the binding affinity of the corresponding proposed ligand molecule using the data of a. and b. to perform each of the following:
  i. computer analysis of the corresponding proposed ligand molecule data to determine whether the corresponding proposed ligand molecule includes at least one $\pi$-conjugated moiety having multiple possible geometries, one of the geometries being characterized by less delocalization of electrons across the $\pi$-conjugated moiety than the delocalization of electrons characterizing another of the geometries, and
  ii. computer analysis of the predicted structure of the ligand-receptor structure which includes determining whether the ligand in the ligand-receptor structure adopts the geometry characterized by less delocalization, and if the ligand adopts the geometry, then
  iii. including in the scoring a penalty for reduced delocalization of electrons across the $\pi$-conjugated moieties, wherein the magnitude of the penalty is an amount indicative of the reduction of electron delocalization between the configuration of the corresponding proposed ligand molecule when complexed with the receptor and the delocalization of an uncomplexed, more delocalized, configuration of the corresponding proposed ligand molecule,
identifying one or more active complexes based on the scored binding affinities for the proposed ligand mol- ecules and the known molecular receptor and discriminating one or more inactive complexes based on the scoring; and testing a proposed ligand molecule of at least one of the identified active complexes.

2. The method of claim 1 in which step c. i. includes determining whether the ligand includes one or more rotatable bond paths connecting two chemical moieties which are capable of significant π electron delocalization between the groups across the rotatable bond.

3. The method of claim 2 in which step c. ii. includes determining the configuration of the corresponding proposed ligand molecule in the a ligand-receptor complex, and, for at least one rotatable bond path identified in step c. i., determining whether the geometry of the docking configuration substantially reduces electron delocalization of an energetically accessible ligand geometry in solution or in the gas phase.

4. The method of claim 1 in which the π-conjugated moiety includes at least one rotatable bond, wherein rotation of the bond changes the extent of delocalization of electrons across the π-conjugated moiety.

5. The method of claim 1 in which the π-conjugated moiety includes at least one aromatic ring.

6. The method of claim 1 in which the π-conjugated moiety is more planar in the configuration characterized by greater delocalization than it is in the configuration characterized by less delocalization.

7. The method of claim 1 in which the energies of the configurations of the π-conjugated moiety are measured by one or more of: a molecular mechanics force field, quantum chemical methods, or deviations from planarity.

8. The method of claim 1 in which clashes between atoms that form internal hydrogen bonds are ignored when scoring the corresponding proposed ligand molecule binding affinity.

9. The method of claim 1 in which the corresponding proposed ligand molecule includes multiple conjugated rotatable bond paths and the method includes assessing a penalty for each bond path when the corresponding proposed ligand molecule in the ligand-receptor structure adopts the geometry characterized by less delocalization.

10. The method of claim 1 in which aromatic atom types composing a π-conjugated moiety are identified, aromatic bond paths within π-conjugated moiety are enumerated, aromatic rotatable bonds lying along these aromatic bond paths are identified, torsion angles of these aromatic rotatable bonds are computed, and a free energy penalty is computed as a function of the torsion angles.

11. A method of screening a plurality of proposed ligand molecules for binding to a known molecular receptor, the method comprising:

for each of a plurality of complexes each comprising a ligand-receptor structure comprising a corresponding one of the proposed ligand molecules and the known molecular receptor, scoring a binding affinity of the corresponding proposed ligand molecule to the known receptor using a computer and computer stored data, wherein the scoring comprises:

a) receiving, by one or more computers, data representing one or more of the proposed ligand molecules to be scored, b) receiving, by one or more computers, data representing a predicted structure of the ligand-receptor structure between the known molecular receptor and the corresponding proposed ligand molecule, c) scoring the binding affinity of the corresponding proposed ligand molecule using the data of a. and b. to perform each of the following:

i. computer analysis of the corresponding proposed ligand molecule data to determine whether the ligand includes at least one π-conjugated moiety having multiple possible geometries, one of the geometries being characterized by less delocalization of electrons across the π-conjugated moiety than the delocalization of electrons characterizing another of the geometries, said computer analysis of the corresponding proposed ligand molecule comprising a determination whether the corresponding proposed ligand molecule includes one or more rotatable bond paths connecting two chemical moieties which are capable of significant electron delocalization between the moieties across the rotatable bond, the determination comprising a conformational search investigating energy of at least one conformation of the corresponding proposed ligand molecule in solution or in the gas phase and to identify a ligand conformation exhibiting conjugation between the moieties connected by a rotatable bond, and ii. computer analysis of the predicted ligand-receptor structure which includes determining whether the corresponding proposed ligand molecule in the ligand-receptor structure adopts the geometry characterized by less delocalization, and if the ligand adopts the geometry, then iii. including in the scoring a penalty for reduced delocalization of electrons across the π-conjugated moieties, wherein the magnitude of the penalty is an amount indicative of the reduction of electron delocalization between the configuration of the corresponding proposed ligand molecule when complexed with the receptor and the delocalization of an uncomplexed, more delocalized, configuration of the corresponding proposed ligand molecule, identifying an active complex based on the scored binding affinities for the proposed ligand molecules and the known molecular receptor and discriminating an inactive complex based on the scoring; and testing a proposed ligand molecule of at least one of the identified active complexes.

12. The method of claim 11 in which the degree of conjugation along the rotatable bond path is determined by the deviation from planarity of the moieties connected by the rotatable bond path.

13. The method of claim 11 in which a molecular mechanics force field is used to calculate the energies of the various conformations in the conformational search.

14. The method of claim 13 in which aromatic atoms are identified and aromatic bond paths are enumerated from the connectivity of the identified aromatic atoms.

15. The method of claim 11 in which quantum chemical methods are used to calculate the energies of the various conformations in the conformational search.

16. The method of claim 15 in which rotatable bonds along aromatic bond paths are identified.

17. The method of claim 11 in which a simplified interaction model, such as one enforcing minimum allowed distances between atoms of various types, and basing the conjugation energy upon deviation from planarity, is used to evaluate the energetics of the various conformations in the conformational search.

18. The method of claim 17 in which clashes between atoms that form internal hydrogen bonds are ignored when scoring the proposed ligand binding affinity.

19. The method of claim 17 in which torsion angles of rotatable bonds are computed.

20. The method of claim 17 in which a penalty is estimated from the value of torsion angles.

21. The method of claim 11 in which the magnitude of the penalty is determined by the degree of distortion of the ligand conformation in the docked complex from the low energy conformation in solution or in the gas phase.

22. The method of claim 11 in which a penalty of zero is assigned to a conjugated rotatable bond path if the lowest energy conformation in solution or in the gas phase does not enable substantial conjugation between the two moieties connected by the conjugated rotatable bond path, due to large deviation from planarity.

* * * * *

UNITED STATES PATENT AND TRADEMARK OFFICE
CERTIFICATE OF CORRECTION

PATENT NO. : 9,858,395 B2
APPLICATION NO. : 13/113506
DATED : January 2, 2018
INVENTOR(S) : Richard C. Friesner et al.

Page 1 of 1

It is certified that error appears in the above-identified patent and that said Letters Patent is hereby corrected as shown below:

In the Claims

Column 11, Line 13, Claim 3, delete "in the a" and insert -- in the --, therefor.

Signed and Sealed this
Third Day of April, 2018

Andrei Iancu
*Director of the United States Patent and Trademark Office*